United States Patent [19]
Goldfischer et al.

[11] Patent Number: 4,839,806
[45] Date of Patent: Jun. 13, 1989

[54] COMPUTERIZED DISPENSING OF MEDICATION

[76] Inventors: Jerome D. Goldfischer, 199 Charlotte Pl., Englewood Cliffs, N.J. 07632; Michael Smith, 86 Harriet Ave., Bergenfield, N.J. 07621; Harvey Goldfisher, 160 E. 38th St., New York, N.Y. 10016

[21] Appl. No.: 913,734

[22] Filed: Sep. 30, 1986

[51] Int. Cl.⁴ ............................................. G06F 15/42
[52] U.S. Cl. ................................ 364/413.02; 364/900
[58] Field of Search ............... 364/415, 401, 403, 900, 364/413.02; 235/385

[56] References Cited

U.S. PATENT DOCUMENTS

| | | | |
|---|---|---|---|
| 4,121,574 | 10/1978 | Lester | 364/415 |
| 4,150,284 | 4/1979 | Trenkler | 364/415 |
| 4,216,462 | 8/1980 | McGrath | 364/415 |
| 4,356,475 | 10/1982 | Neumann | 364/415 |
| 4,415,802 | 11/1983 | Long | 235/385 |
| 4,476,381 | 10/1984 | Rubin | 235/385 |
| 4,513,295 | 4/1985 | Jones | 364/415 |
| 4,530,067 | 7/1985 | Dorr | 364/401 |
| 4,546,436 | 10/1985 | Schneider | 364/415 |
| 4,685,059 | 8/1987 | Yamamoto | 364/415 |

Primary Examiner—Jerry Smith
Assistant Examiner—Gail O. Hayes
Attorney, Agent, or Firm—Frishauf, Holtz, Goodman & Woodward

[57] ABSTRACT

A technique for providing automated direction and guidance to nurses to assist in the task of dispensing medication to patients. Information on all patients is stored in a stationary base computer. Information pertinent to the medication dispensing task is transferred from the base computer to a portable, hand-held computer adapted to be carried by the nurse during rounds. One portable computer contains information for only those patients assigned to one nurse. As the nurse approaches a patient, the portable computer is activated to display the name of each medication to be dispensed to that patient along with dose, route, and comments. The nurse enters into the portable computer whether the medication was dispensed or not. It can, thus, be determined whether any medication remains to be dispensed, and why it has not yet been administered. At the completion of rounds, data is transferred from the portable computer to the base computer to update the information stored in the base computer.

84 Claims, 4 Drawing Sheets

COMPUTERIZED DISPENSING OF MEDICATION

BACKGROUND OF THE INVENTION

This invention is directed to a technique for providing automated direction to nurses for dispensing medication to patients and, more particularly, to a technique for storing patient information and medication-dispensing instructions in a main computer from which that information and instructions pertinent to designated patients are retrieved and transferred to a portable, hand-held unit that is carried along by the nurse on medication rounds to direct the task of dispensing medication.

Hospitals now use a system for dispensing medication to patients which is prone to error. It is a multi-step, cumbersome, labor intensive, repetitive, and time consuming approach which relies on hand-written instructions, hand-written reports, periodic hand-written changes by way of erasures and/or additions, verbal communication, and manual sorting of large amounts of data. Specifically, the overall process includes the following steps.

At admission, the patient is questioned to obtain personal information as well as his medical history. After a medical examination, the doctor completes an order sheet which lists the drug, dosage, route (e.g., IV, injection, oral) and frequency in which the drug is to be given. A nurse at the main nursing station takes the order sheet and combines it with any other information she has about the medical history of the patient such as allergies, contra-indications, and the like, to prepare a medication summary record for that patient. When a medications nurse comes on duty, a set of patients is assigned to that nurse. The nurse pulls the medication summary records for these patients and prepares hand-written notes to assist in correctly dispensing the proper medications on the next medication round. As the nurse dispenses the medication, the notes kept by the nurse are marked according to what occurred. For example, the patient may have refused the medicine, or he may have been away from the room in which case the medication was missed. Upon returning to the main nursing station, the nurse uses the notes to update the medication summary record. These notes are then utilized by the same nurse or another nurse for the next medication dispensing round.

It can readily be seen that each time medication information is written by hand, it is potentially a source of error. With the above-described approach, such information must be written and rewritten many times over. The medication summary record is initially written. The medication nurse prepares notes from this record. Also, the record is manually updated when a round is completed. This is repeated for each and every medication dispensing round in each and every day. Thus, the information is susceptible to error in the course of such multiple hand-written transfers of information. Furthermore, the instructions ordered by the physician are subject to change periodically. These changed instructions are typically written at the bottom of the medication summary record. This can be an extremely messy operation, complicates the task of reading and understanding the medication summary record and is a potentially significant source of error. Moreover, a medication summary record is good for no longer than 7–10 days because of the limited space on the sheet. Thus, it has to be recopied for the next period. Finally, medication instructions ordered by a physician are only good for a certain number of days. The instructions must be renewed or cancelled at the termination of that time. This information must be entered manually again. The overall system can be, therefore, messy, awkward, time consuming, and, most importantly, far from the reliable system which one expects to exist when so much is at stake.

This system replaced and updated a prior method in which a colored card technique was used which had a different colored card related to a particular time of day. The information on cards of a particular color was, therefore, restricted to an assigned time of day. Therefore, confusion about medication dispensing times is minimized. However, much of the criticism applied to, and the dissatisfaction with, the above-described system was applicable to this approach as well.

Some hospitals have installed a more modern computerized system which stores patient information as well as the doctor's medication dispensing instructions in a data base. The medication nurse can access the data base to retrieve pertinent information about her designated set of patients from which she prepares her own notes for carrying out the task. It may also be possible to obtain a set of medication dispensing instructions from the computer itself. However, even this approach is unsatisfactory because during rounds the nurse makes hand-written notes regarding the dispensation of the medicines, as explained above. With this method, medication can be given to the wrong patient, missed, or passed over. At the completion of the rounds, the nurse must take those notes and either update the data base or convey the information to someone else for updating the data base, thereby exposing a further possibility of posting error. The hand-written operations involved at these stages of the overall task can also be significant sources of error. Specifically, if the information is not written or recognized properly, then a missed medication may not be noticed. Also, medication might have been dispensed but listed as missed in which case unnecessary medication might be administered to the patient. Furthermore, the system does not include any check on the nurse's actions to monitor during the actual rounds that the correct medication is being dispensed. For example, in reading down the list of notes kept by the nurse, it is possible to inadvertently interchange the medication instructed for one patient with that of another and, consequently, the wrong medication will be administered.

A further deficiency of these prior art approaches lies in the incompatibility between the instructions for dispensing medication and the task of obtaining medication from the hospital pharmacy. Forms must be filled out and conveyed to the pharmacy where, possibly, other forms must be completed to retrieve the requested medications and ship them to the correct hospital floor. Further forms must be completed for inventory control and for billing. Each of these requires multiple steps involving hand-written operations, all of which are potential sources of error. Moreover, efficiency is compromised and this tends to raise hospital costs.

SUMMARY OF THE INVENTION

It is a primary object of the invention to provide a medication dispensing system which improves the accuracy and reliability with which medication is administered.

Another object of the invention is to provide a computerized medication dispensing system to eliminate the need for hand-written recording of information.

A further object of the invention is to provide a medication dispensing system which directs and guides the task of dispensing medication as it is being performed to improve the accuracy and reliability with which medication is administered.

Yet another object of the invention is to provide a medication dispensing system which improves the efficiency of the various operations involved in ordering, keeping in inventory, billing and dispensing medication.

These and other objects of the invention are attained by a method for dispensing medication comprising the steps of storing, for each patient, patient information, such as the name of the patient, which is relevant to the dispensing of medication; storing for each patient medication information, such as the name of the medication, which is directly required for the dispensing of medication; such patient information and such medication information being stored into a memory of a stationary base computer; retrieving from the memory at least some of such patient information and such medication information for designated patients; transferring such retrieved patient information and such retrieved medication information to a portable computer adapted to be carried by a nurse assigned the task of dispensing medication to such designated patients; and selectively prompting the nurse with the portable computer, such as by patient name and by medication name, to dispense medication to at least one of the designated patients.

Another aspect of the invention is directed to a method for dispensing medication comprising the steps of: storing, for each patient, patient information such as the name of the patient which is relevant to the dispensing of medication; storing for each patient medication information, such as the name of the medication, which is directly required for the dispensing of medication; such patient information and such medication information being stored into a memory of a portable, hand-held computer adapted to be carried by a nurse assigned the task of dispensing medication to the designated patients; and selectively prompting the nurse with the portable computer, such as by patient name and by medication name, to dispense medication to at least one of the designated patients.

A further aspect of the present invention is directed to an apparatus for guiding a nurse in the activity of dispensing medication comprising: means for storing, for each patient, patient information such as the name of the patient which is relevant to the dispensing of medication; means for storing for each patient medication information such as the name of the medication, which is directly required for the dispensing of medication; such patient information means and such medication information means being comprised in a memory of a stationary base computer; means for retrieving from the memory at least some of the patient information and the medication information for designated patients; portable computer means adapted to be carried by a nurse assigned the task of dispensing medication to the designated patients; means for transferring the retrieved patient information and the retrieved medication information to the portable computer means; and means in the portable computer means for selectively prompting the nurse with the portable computer, such as by patient name and by medication name, to dispense medication to at least one of the designated patients.

Yet another aspect of the present invention is directed to an apparatus for dispensing medication comprising: means for storing, for each patient, patient information such as the name of the patient which is relevant to the dispensing of medication; means for storing, for each patient, medication information, such as the name of the medication, which is directly required for the dispensing of medication; such patient information means and such medication information means being comprised in a memory of a portable, hand-held computer adapted to be carried by a nurse assigned the task of dispensing medication to the designated patients; and means in the portable computer for selectively prompting the nurse with the portable computer means, such as by patient name and by medication name, to dispense medication to at least one of the designated patients.

In addition to the above-described aspects of the invention, the invention also provides for entering the status of each scheduled medication as to whether or not it was dispensed. This enables a determination of which medications have not been dispensed. It is also possible to enter the reason for not having administered the medication, such as refusal by the patient, absence of the patient from the room, or a condition of the patient which was indicated by the doctor to be one when this medication should not be administered. The nurse can obtain a listing on the screen of the portable computer of all such undispensed medications together with the reason each was not administered. The nurse can then decide whether to try again with a particular patient, or whether to skip administering a particular medication to that patient during the rounds in progress.

Information entered into the portable computer is transferred to the base computer to keep the main data base on each patient complete and current in the base computer. This data is then used for later rounds, for spot checks by the doctor and/or charge nurse, and for administrative reasons to maintain long term records.

In order to minimize the potential for mixups between patients assigned to particular medication nurses, a nurse verification procedure is performed. A confidential code unique to one nurse is entered into the portable computer. Unless the nurse enters this code, the portable computer will not function properly. Furthermore, in order to insure that no mixup occurs between patients, the nurse approaches a particular patient and enters into the portable computer a patient identification code from that patient's wrist bracelet. The computer then responds by displaying the patient's name. If the correct name is displayed, then that patient's identity has been verified.

With the nurse being guided in the medication dispensing task by a computer carried along on rounds, no handwritten notes are used which might cause mistakes of omission and commission. Clear and definitive data is presented to the nurse on the screen of the portable computer for each patient. Furthermore, the information is up-to-date because changes are entered electronically to reflect new instructions and/or circumstances. Also, the portable computer enables the nurse to quickly and conveniently check whether any medications scheduled for the rounds in progress have not yet been administered, and if any have not been, for what reason. A clear picture is thus available to the nurse in accurate, uncluttered and easy to read form at all times to check on what has not been done. In accordance with one advantageous aspect of the invention, information on any missed medications in one rounds is carried over to the next rounds so that such missed medications can then be dispensed.

In accordance with another advantageous aspect of the invention, information on patients and medications stored in electronic form per the above is used to assist the pharmacy and the billing department. When a particular medication is prescribed and entered into computer memory, that information is transmitted electronically to the pharmacy. Such information can then be used to distribute the needed medications and to continuously maintain inventory information current. Also, the quantity and location of controlled substances can be tracked easily. As to billing, information on medications actually dispensed to a given patient is also part of the data stored in computer memory. This can be incorporated into the total bill to charge for medication used.

DETAILED DESCRIPTION OF THE PREFERRED EMBODIMENTS

A patient may resort to any one of a variety of different types of available medical care facilities. Such a facility can, of course, be a hospital, but it can also be a clinic, nursing home, convalescent facility, emergency room, out-patient facility, or even a doctor's office where the individual may need to stay for less than a day. For the purpose of this invention, the facility and type of care provided by it to the patient are relevant only insofar as they concern the need to dispense medication of some sort to a patient who is under the care of that facility. The forthcoming description of the invention presumes that medical care is provided in a hospital because it typically provides the most comprehensive services, and the system of this invention has been designed to accommodate it. Of course, once a system has been devised to be comprehensive, it can also be simplified to function satisfactorily in another type of medical care facility, such as a clinic. For the sake of simplicity, all available medical care facilities which dispense medication will be referred to under the term "hospital".

When a patient is first received in the hospital, data is obtained directly from him about certain personal characteristics. (The words "information" and "data" are used synonymously and are interchangeably throughout the Specification). Examples are name, address, age, hospital identification number such as social security number, insurance carrier, name of doctor, allergies, etc. A suitable form is completed by the patient or by someone in the reception office with this information plus other relevant information, such as the hospital chart number, building name, and the room number to which the patient is assigned.

A nurse (this term is used figuratively to describe a responsible person assigned to the about-to-be described tasks. Although the feminine gender is used, this is done solely as a matter of convenience and with the realization that it is not accurate in describing all nurses) on the hospital floor to which the patient has been assigned receives the form upon the patient's arrival on that floor. In accordance with the invention, the nurse selects certain needed information from the form and enters it into the data base of a computer. A stationary computer of any suitable type can be used for this purpose. It requires enough storage capacity to handle the information pertinent to the care of all the patients on that floor, as well as the capability of manipulating, displaying and transmitting that information in the manner provided for by the present invention, as discussed in detail below. The preferred computer is an IBM PC supplied with a hard disk and a floppy disk. Such computers are already widely known and in common usage in offices, industry and academia. Thus, it is believed that no further details are required. In the ensuing discussion, this computer will be referred to as the "base computer".

Figure 1:
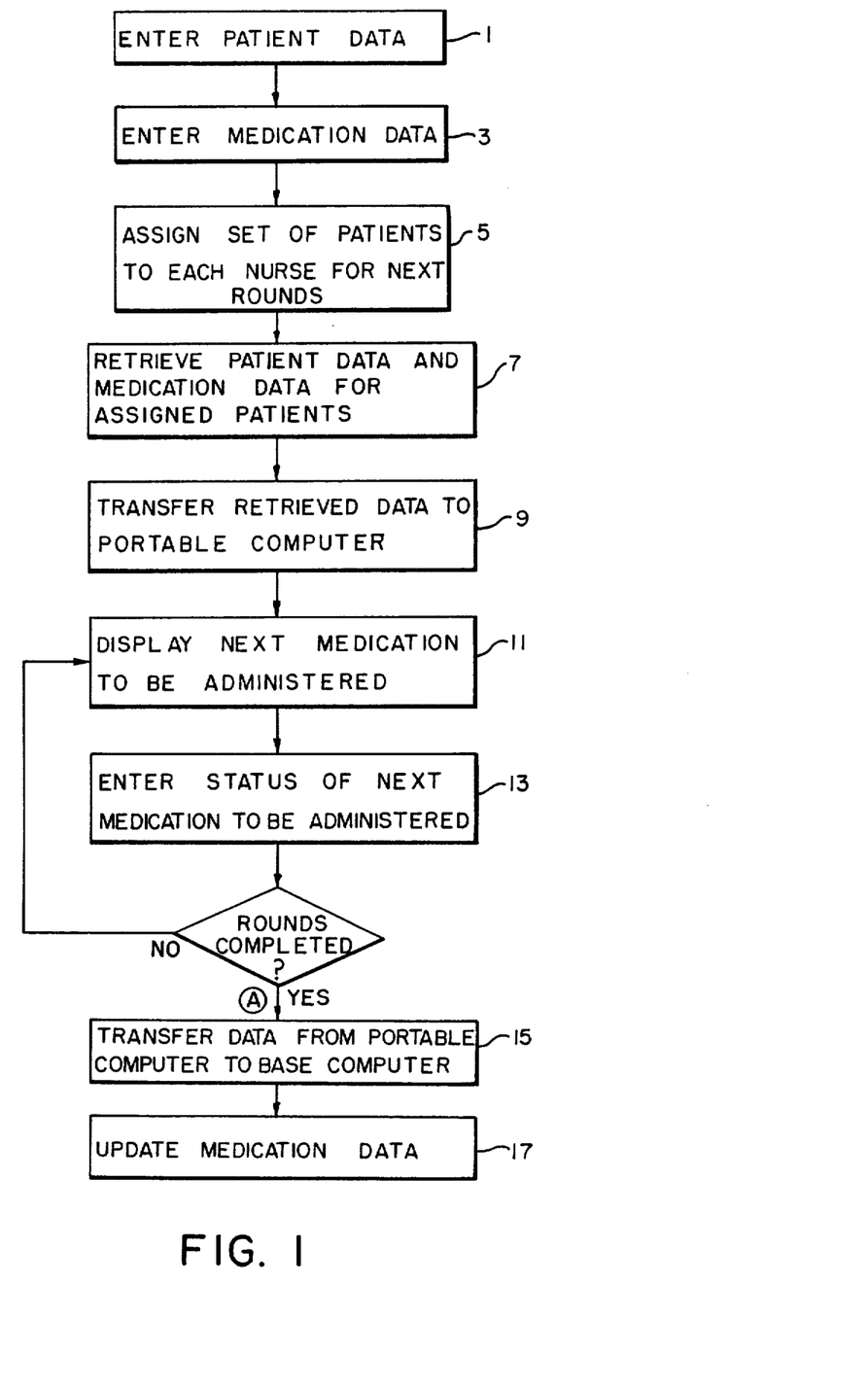
FIG. 1 is a flow chart showing the basic operations utilized in the technique of the present invention.

For the purposes of the invention, and in accordance with box 1 of FIG. 1, the nurse need only enter into the base computer the following patient information: name, social security number, room number, type of patient (e.g. critical, outpatient, or alternate care), name of doctor, and allergies. This information is stored in dedicated locations of the computer memory which are commonly known as "fields". Each category of information is assigned its own field. Thus, information retrieval is performed in an orderly fashion, and it is possible to retrieve only certain fields when others are not needed.

After the doctor has examined the patient and decided to prescribe medication(s), the doctor writes a medication order which includes such information as the drug name, start date, end date, dosage, dosage frequency, route (e.g. oral, injection, IV), and other specific instructions which are to be considered by the medication nurse in deciding whether to administer that medication at a certain time, such as when the patient's temperature is elevated or upon request from the patient. Alternatively, the doctor enters data based on prompting from the base computer on its monitor. For example, a list of medications can be displayed, and the doctor selects electronically from this list in any one of several well known ways. One possibility is to move the cursor to the desired medication and then touch a key on the keyboard, such as RETURN.

In accordance with box 3 of FIG. 1 (and assuming the doctor writes the medication order), this medication information is converted by the nurse into computerized information by entering it into the base computer. Fields are also assigned to the medication information so that each has its own dedicated field for the purposes discussed above in connection with the patient information. Extra fields are also assigned for categories such as time medication last given, and date medication last given. The need for these fields is explained below.

With operations 1 and 3 having been performed for all of the patients assigned to a given hospital floor, all the available above-described data in the various fields is now stored in computer memory for use in the manner described below in accordance with the invention.

Each floor has a number of nurses performing rounds at any given time. Also, different nurses come on duty in shifts throughout the day. Each nurse is in charge of caring for a certain number of patients. A charge nurse is responsible for dividing all the patients on her floor among the on-duty nurses available for rounds. Thus, she determines that nurse A will serve as a medication nurse and care for Patients 1-10. In accordance with box 5 of FIG. 1, the charge nurse proceeds to enter into the base computer a list of certain patients whom she has selected to place under the care of a certain medication nurse. This can be done by assigning certain rooms to nurse A which include Patients 1-10 or, alternatively, by picking out individual patients because, for example, even though the assigned patients may not be conveniently grouped in adjacent rooms, the assigned patients in dispersed rooms require the special training of nurse A. Development of the computer program to enter a list of patients with their corresponding nurse, storing this data as related information, and retrieving it involves a straightforward operation the details of which are not needed and would only obscure the essential features of the invention.

Each duty nurse charged with the task of dispensing medication is provided with a light, portable computer sized to fit conveniently into the nurse's hand. The portable computer must have a memory capacity sufficient to handle the patient data and medication data for the number of patients the hospital typically assigns for rounds to each medication nurse. In the present example, this number is ten patients. A display screen is required as part of the portable computer so that it can visually provide needed information to the nurse. Also, various control and information entry keys are necessary. Finally, the portable computer must have the data processing capability called for by the present invention for conducting the operations described in detail below. Such portable computers with the requisite "power" and memory capacity are readily available. A preferred model is manufactured by Melard Technologies, Inc. of Elmsford, New York under the trademark Access.

After the charge nurse has assigned all the patients under her responsibility to medication nurses by, say, room number, the data pertinent to the patients is retrieved from memory, per box 7, nurse by nurse. Data on all the patients assigned to one nurse is then loaded, per box 9, to a portable computer. The data is loaded along with a three-digit code, for example, uniquely identifying the nurse. This is repeated until as many portable computer units have been loaded in this manner as the number of medication nurses doing the next rounds. Thus, each nurse is given a portable computer into which data on only patients assigned to that particular nurse has been stored.

Information is transmitted in accordance with the invention between the base computer and each portable computer via a suitable line which connects these two units to each other. Such a connection is made by the nurse in charge of transferring the data either when she first approaches the base computer or when the retrieval of assigned patients is completed by the base computer in accordance with the operations in box 7.

Following such transfer, the line is removed from at least the portable computer so that it can readily be carried by the nurse during her rounds. The portable computer has been loaded and is now ready to be carried by the nurse during rounds for approaching each of the assigned patients and dispensing the prescribed medications.

Along with loading the portable computers with data from the base computer, this task can include printing a "pre-rounds report" which lists the assigned patients and the hours medication is to be given for each patient. Individual medications need not be listed. Also listed in the pre-rounds report are those assigned patients with IV solutions running, and the estimated times those solutions are to be changed. Controlled medications can also be listed by name and dose to allow the nurse to conveniently obtain these at the beginning of rounds from a locked cabinet. This report is, therefore, a convenient summary for the nurse which aids in previewing the upcoming activity and in planning how best to carry it out.

When nurse A comes on duty, she is given the portable computer which has been loaded with Patients 1-10 assigned to her. She is also given the pre-rounds report. Further details on the preliminaries performed before the beginning of rounds are provided below in connection with the discussion of FIGS. 2 and 3.

Continuing with the general explanation of the invention with regard to FIG. 1, as the nurse proceeds on her rounds from patient to patient, the portable computer displays the required patient data such as name and identification number (i.e. social security number) along with all prescribed medications which must be given during that particular rounds. This sequence of operations is depicted by box 11 of FIG. 1. During this stage, the portable computer displays information to guide, assist, and verify the nurse's actions in dispensing medication.

As the nurse administers each medication which has been displayed for her on the face of the portable computer in accordance with the present invention, she also must enter status data as to what resulted from her efforts to administer medication to a particular one of Patients 1-10. The status data can be REFUSE—meaning the patient refused the medication, GIVEN—meaning the dosage was normally administered, HOLD—meaning the nurse decided not to administer the medication for some reason, such as elevated temperature, and NOT GIVEN—meaning the patient was unavailable for some reason, such as being in the X-ray department. The ENTER button is depressed to store the information selected by touching one of the keys 100-105 shown in FIG. 4 and further discussed below.

After the status data is entered by the nurse, the portable computer searches through its stored data base to determine whether any more medications need to be dispensed at this time. This is represented by decision box 14. If it determines that at least another medication is scheduled for this round, it will route the program back to box 11.

Operations 11 to 14 of FIG. 1 are explained in greater detail by FIGS. 2 and 3 and the corresponding discussion found below.

After nurse A has completed her rounds and tended to each of Patients 1-10, the portable computer is carried back to the base computer. Information must be transmitted from the portable computer to the base computer. The two computers are re-connected to each other via an above-mentioned line. When this is done, the nurse depresses an appropriate key on the keyboard of the base computer which actuates the required transmission of data from the portable unit to the base computer, per box 15. Information retrieved in this manner from the portable computer is utilized, per box 17, to update the various fields resident in memory of the base computer and mentioned above as dedicated to a particular category of information. Thus, for example, the medication status field is updated with the data entered during the just-performed rounds. Likewise, the timelast-given and the last-date-given fields are updated with the latest information from the just-completed rounds. This updated information will, in turn, be utilized for nurse B who will perform the next rounds in the same manner as described above, and yet to be described below, for nurse A.

Figure 2:
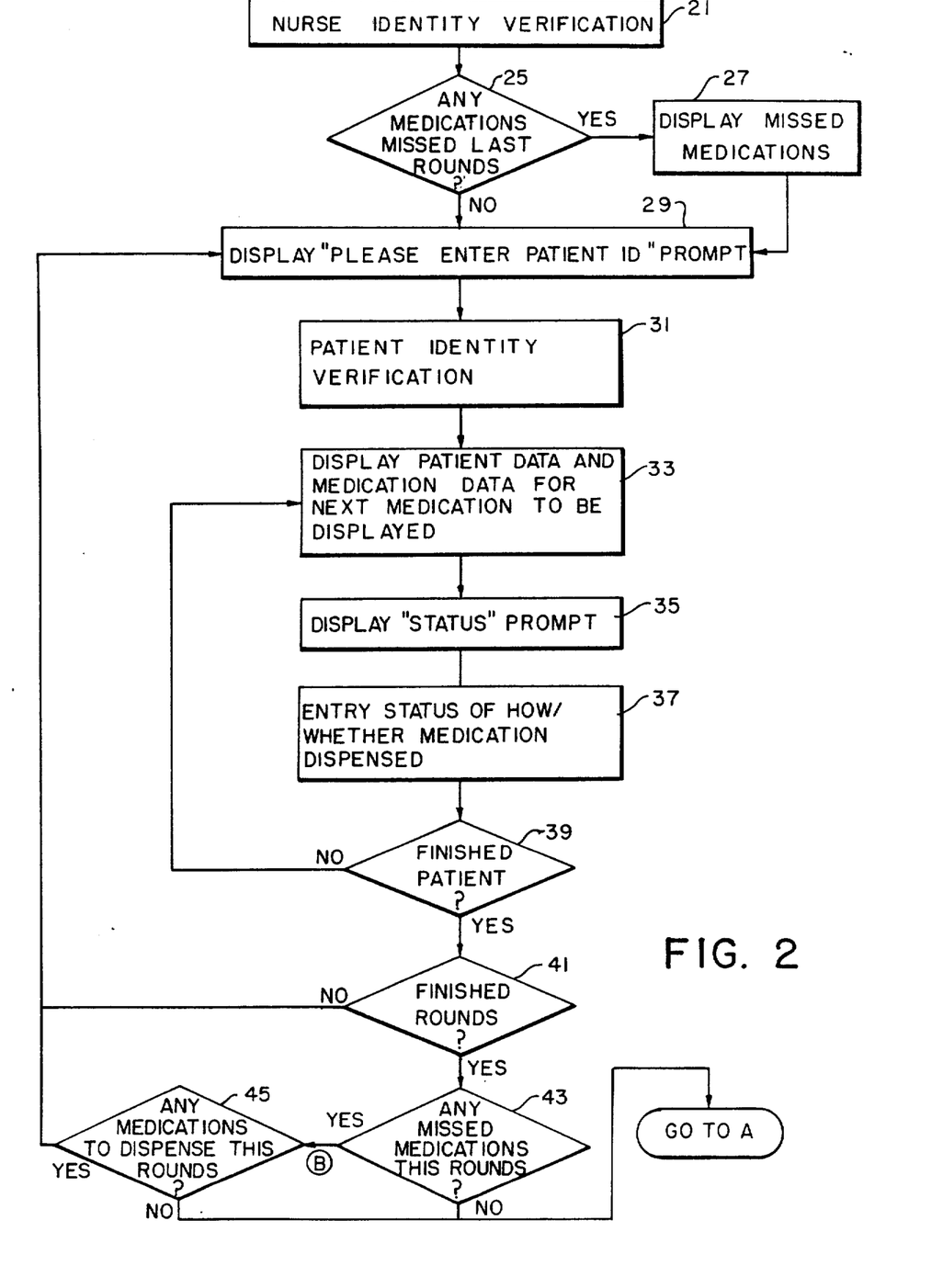
FIG. 2 is a flow chart showing the operations performed by the portable computer hand-held by the nurse during rounds.

Turning now to FIG. 2, it describes the various subroutine operations corresponding to the routine depicted in boxes 11, 13 and 14 of FIG. 1. Specifically, after the relevant patient data and medication data have been transferred to the portable computer by operation 9 of FIG. 1, operation 11 is begun by nurse verification operation 21. It is advisable to include such a step for purposes of reliability and security so that the portable computer is rendered unusable unless the correct nurse is using it. If, for example, portable computers have been loaded for several nurses with data retrieved from the base computer and are stored at the same location, it is not inconceivable that inadvertently the portable computers may be interchanged. The verification is done electronically with the above-mentioned three-digit identification code stored in the base computer and which the base computer has downloaded to the portable computer.

Each nurse has a unique code. For example, nurse A might have code 101. This code is also needed to keep track of which nurse dispensed the medication to certain patients at certain times. Such information may be required by the hospital administration and/or for legal reasons in case something goes wrong which is traceable to the medication. When the portable computer is turned on, it prompts the nurse for the nurse identification number after the ENTER button is depressed. If the entered number does not match the stored number, the portable computer will not respond to keyboard manipulations and the display will again show a prompt asking for the identification number. If the correct number is entered by the nurse, the display will read, for example, "good morning Miss Jones". No further details are necessary regarding this type of verification procedure as it is believed to be in general use and widely known.

Once it has been established that the correct unit has been given to nurse A, the portable computer is taken by nurse A and can be turned OFF for a time until the nurse is about to embark upon her rounds. The nurse may need to take some time to review the pre-rounds report, get a verbal report from the prior nurse, start her other daily activities, etc. When the nurse is ready to start her rounds, the portable computer is turned ON, and the verification process is again conducted to "unlock" the operation of the portable computer. That being done, the portable computer can then be put through its paces.

As part of the previous rounds, a list of medications missed during the previous rounds had been compiled, as explained below. This information had been stored in the base computer at the end of such previous rounds. As part of the data retrieval operation in box 7 of FIG. 1, the base computer executes a routine for determining whether any medications were missed during the last rounds. Such missed medications are collected, patient by patient, and downloaded by operation 9 (FIG. 1) to the portable computer. As soon as the above-described nurse verification procedure is completed, nurse A touches QUERY and then ENTER on the portable computer, per box 25, to determine whether any medications were missed in the last rounds. The portable computer responds, per box 27, by denoting the missed medications from the previous rounds with an asterisk. All these can be displayed together by the portable computer, or as part of the medications to be dispensed arranged and displayed separately for each patient. The nurse can decide whether the patients with the missed medications need to be looked after first, or whether these missed medications can be administered during the normal rounds routine.

To begin the steps leading to dispensing medication, the ENTER button is touched to access the operation described with regard to box 29.

Figure 4:
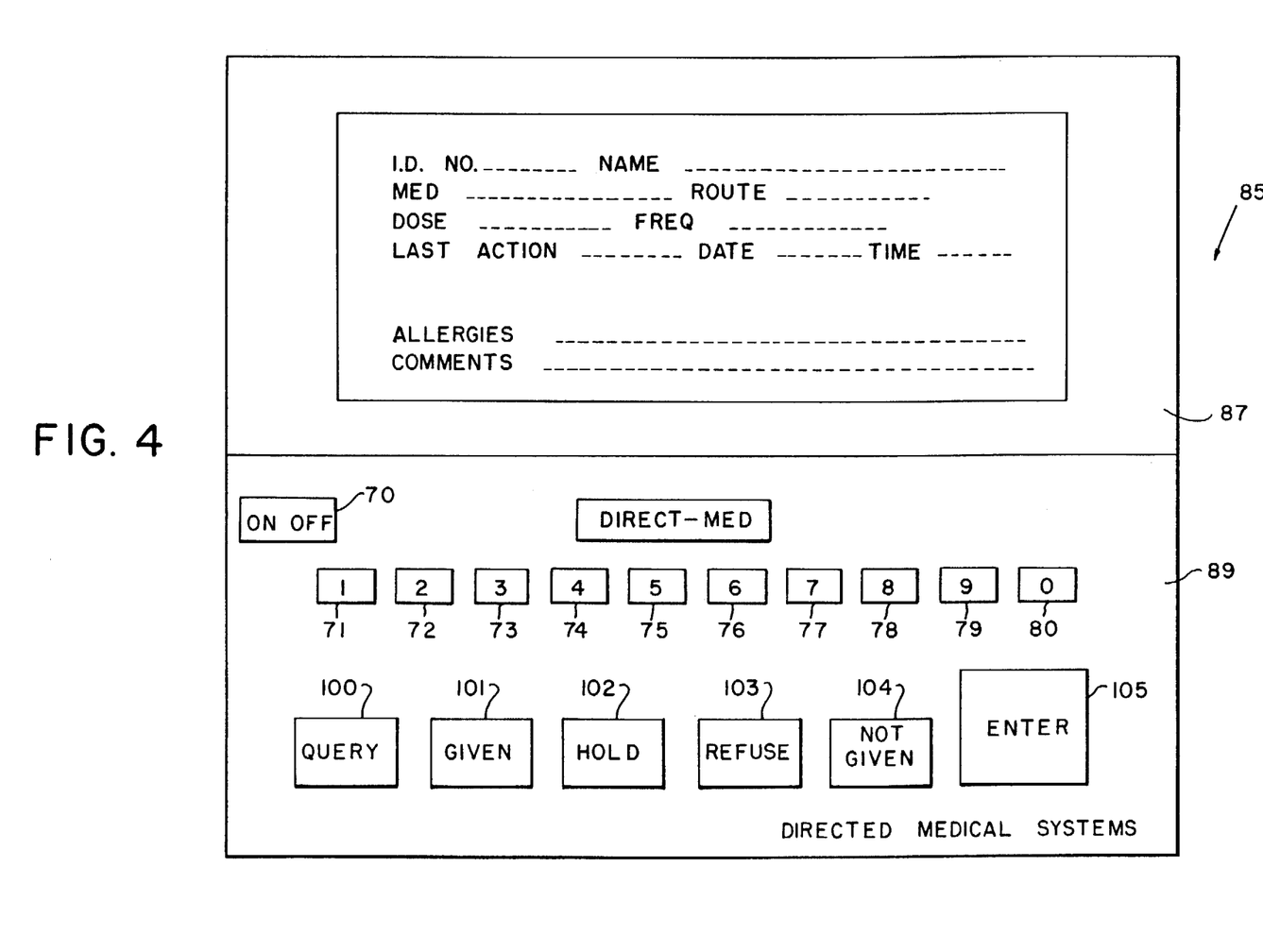
FIG. 4 depicts the face of the portable computer showing the display area as well as various input and control keys.

If routine 25 determines that no medications were missed during the previous rounds and, therefore, no asterisked medications appear on the display, nurse A touches ENTER and the program proceeds directly to box 29 which displays the prompt "please enter patient ID #". This instructs the nurse to go to the next of her ten patients. If her rounds have just begun, then the nurse will proceed to the first room on the pre-rounds report, for example. From the wrist bracelet worn by a patient in that room, nurse A enters the patient identification number typed on it. This is depicted by operation 31. From the patient identification number entered in this manner, the portable computer responds per operation 33 by identifying the patient corresponding to this identification number by name and displaying it. To confirm identify, the nurse checks the displayed name against that which appears on the wrist bracelet. As depicted in FIG. 4, the display shows the patient's name along with the identification number in the first line.

Also displayed on the portable computer per box 33 is medication information pertinent to the patient. The second line of the display lists the name of the medication and the route by which it is to be administered. The following line displays the dosage and its frequency, while the next line shows when the last action was taken for that particular medication. Space is also available to display information on allergies, which might include a warning that the patient is allergic to penicillin, as well as comments such as directing the nurse to administer the drug only if the pulse is above 60 beats per minute.

If the patient name displayed by the portable computer matches that printed on the patient's wrist bracelet, the patient is considered verified. With the patient being verified the nurse proceeds to administer the medication already displayed on the screen. If, however, the patient is not verified, then a data check must be conducted at the base computer. No further details need to be provided on this eventuality.

The screen display also includes a prompt per box 35 for the nurse to enter the "STATUS" for the dispensed medication. This reminds the nurse that after the drug is administered, or an attempt has been made to administer it, the result must be entered. This prompt is, for example, a blinking cursor in the left-hand corner of the display. If the drug is administered, the nurse presses the "GIVEN" key 101 and then the "ENTER" key in order to enter that status into the data base of the portable computer per box 37. "GIVEN" is then displayed in the "Last Action" field on the display screen. Any of the other status keys is, of course, available to enter the appropriate data. Thus, if, for example, the pulse is below 60 the nurse touches the HOLD key 102 to indicate that the medication was not dispensed. Likewise, if the patient happens to be out of the room for whatever reason and, therefore, not available to receive the medication on this rounds, the nurse will touch the NOT GIVEN key 104 to so indicate. Occasionally a patient will refuse taking a medication, and in that case the nurse will enter the REFUSE status by touching key 103. Thus, after the medication dispensing operation has been completed, the portable computer will carry in its memory the required information for later determining whether and why the medication was either dispensed or not.

After the nurse completes this operation for one medication for Patient 1, for example, the portable computer will enter routine 39 to determine whether this patient is to receive any other medications. It thus determines whether the nurse has finished with dispensing medication to this patient. It searches its data base to see whether any of the other medications assigned to this patient are stored in its memory. If it determines that more medications are to be administered to Patient 1, the program automatically returns to operation 33, and the next medication for Patient 1 is displayed. In like fashion to the procedure described above, the program displays the STATUS prompt for the nurse as a reminder that entry of this information is required, and it is entered per the operation depicted by box 37. The program then again returns to box 39. If at the output of box 39 it is determined that Patient 1 has been finished, i.e. no further medications are to be dispensed to him in this round, the portable computer displays the message "all medications for (name) ID #_ have been dispensed. If all entries are correct, touch ENTER; if entry change needed, touch QUERY".

If ENTER is touched, the portable unit proceeds to operation 41 and, if this rounds is to continue, prompts "please enter patient ID #" thus directing nurse A to continue on to the next patient. If, however, QUERY is touched, the portable unit lists sequentially all the just-dispensed medications for this patient along with the STATUS entry made previously. For each medication the portable unit prompts "if entry is correct, touch ENTER; if entry is not correct, touch correct entry and then touch ENTER".

When Patient 1 is "finished" by nurse A, operation 39 answers YES and directs the next step to box 41. Routine 41 determines whether any other patients need to be attended to by the nurse in the current rounds in progress. If it is determined that there are more patients to whom medication needs to be dispensed, then the question "FINISHED ROUNDS?" will be answered in the negative and the program will return to operation 29 for displaying to the nurse the prompt "please enter patient ID #". That patient is then handled in the same fashion as described above by proceeding through operations depicted by boxes 31, 33, 35, 37, and 39. If, however, it is determined that all of the patients assigned to nurse A have been handled by the nurse on this rounds, then the question "FINISHED ROUNDS" is answered positively, and the message "END OF ROUNDS" is displayed. Also, the operation per routine 43 is carried out.

In operation 43 it is determined whether nurse A missed administering a medication to any of Patients 1-10 during this rounds. It is triggered by pressing QUERY followed by ENTER. How this operation is done is explained in greater detail in connection with FIG. 3. Suffice it to say at this point that if the nurse accidentally skipped a patient because he may have been out of the room, or passed a patient because he may have been out of the room, routine 45 then determines whether any medications need to be dispensed in this rounds. In other words, it will show that medication was "NOT GIVEN" to Patient 5 because he may not have been in his room. In such a case, the nurse will then proceed to Patient 5 and continue with the operation depicted by box 29 and the ones following it to administer medication to Patient 5 if, of course, he has returned to the room. However, when the status "HOLD" or "REFUSED" is displayed, the nurse decides whether to return to that patient. If the patient had, for example, been adamant in refusing the medication, the nurse may decide it's best not to return. However, if she feels that it was a fleeting refusal, then she may wish to return to the patient and try again. Similarly, if she held the medication because, for example, the pulse was only slightly below 60, she may wish to return to check whether the blood pressure has dropped.

Thus, routine 45 is a check on the nurse's actions as well as a guide to help her complete her tasks. Since errors of omission are inevitable, the nurse may have skipped a patient. This sequence carried out with the portable computer will catch that omission. Also, even if the omission had been made deliberately, such as in a "HOLD" situation, this invention reviews for the nurse all other actions taken during that rounds to give her an opportunity to take any corrective steps which may be appropriate for that set of circumstances.

If the patient is available and nurse A feels he should be attended to for administering medication previously skipped in the rounds, she touches ENTER and proceeds to that patient where she sequences through steps 29, 31, 33, 35, 37 and 39. Nurse A must enter the updated status or confirm the one previously entered. If the latter occurs, that confirmed entry indicating that medication was not dispensed is then classified as a "MISSED" medication. It will be so recognized by the base computer and later used to form the basis for sorting on this field for the operation depicted at the start of rounds per box 25 and discussed above. In other words, the MISSED medications for rounds #1 are stored in the base computer at the end of rounds #1. When rounds #2 is to be conducted, the MISSED medications are retrieved by the base computer as part of operation 7 and transferred to the portable computer as part of operation 9. The MISSED medications for rounds #1 are then displayed for nurse A in operation 25 performed at the beginning of rounds #2.

The portable computer continues displaying the prompt in box 29 as long as it finds any medications which have not been dispensed and which have not been classified as "MISSED" medications. Touching the QUERY key and then ENTER continues the display of medications not yet dispensed. When all medication has been dispensed except for those classified as "MISSED" medications, the portable unit will display the message "END OF ROUNDS"; or when the nurse determines that rounds cannot be completed, touching the QUERY key followed by "9, ENTER" terminates the rounds and also results in display of the "END OF ROUNDS" message.

If routine 43 reveals that no medications were missed during this rounds, then this sub-routine exits and proceeds to point "A" at the input to operation 15 in FIG. 1 for carrying out the transmission of data from the portable computer to the base computer.

Figure 3:
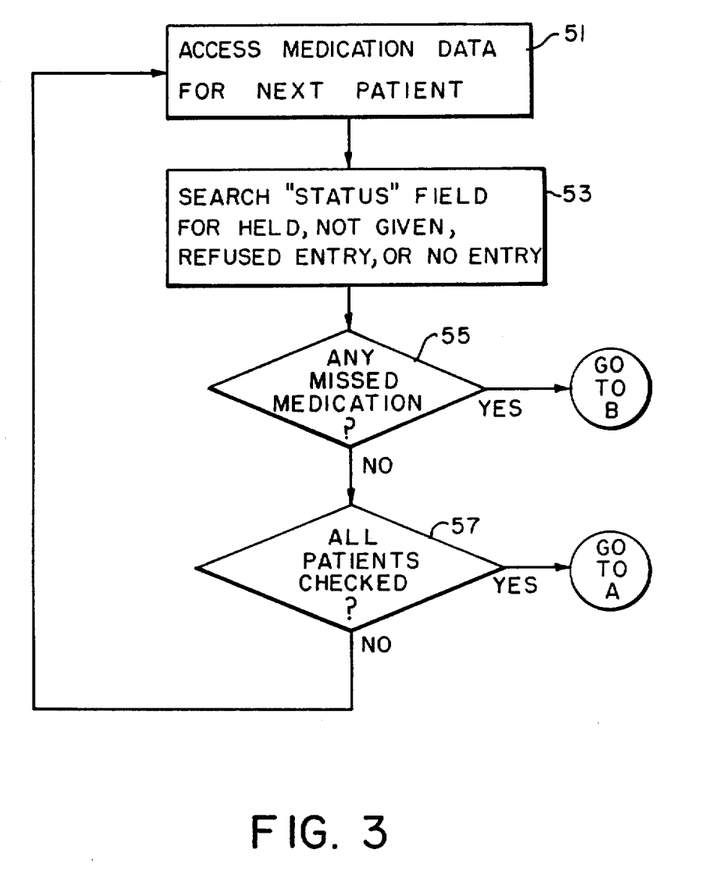
FIG. 3 is a detailed flow chart of part of the FIG. 2 flow chart showing the operations performed to determine whether any medications were missed, i.e. not dispensed, during rounds.

FIG. 3 shows a sub-routine for performing the "MISSED" medications determination. It is initiated by touching QUERY followed by ENTER. As a result, the medication data for each of Patients 1-10 is scanned per operation 51. The "STATUS" field is searched to determine whether the entry in it is for "HOLD", "NOT GIVEN", or "REFUSED". If one of these has been entered by the nurse, or if no entry at all has been made into this "STATUS" field, this patient will be displayed by name along with the missed medication. The search through the data base is depicted by operation 53, and a determination of whether the "STATUS" field includes the data being looked for is made by sub routine 55. If it is determined that a medication has not yet been administered for this patient during the rounds in progress, then the routine proceeds to point B at the input to box 45 in FIG. 2. If operation 55 determines that all stored medications for the rounds in progress were administered to Patient 1, then the operation in box 57 determines whether all the patients have been checked by the subroutine. If not, then the subroutine returns to operation 51 for Patient 2. This procedure continues looping through until all the ten patients have been checked. When all of Patients 1-10 have been reviewed in this manner, operation 57 returns the routine to point A at the input of operation 15 in FIG. 1 for enabling the transmission of information from the portable computer to the base computer, as discussed in detail above.

FIG. 4 shows the face of portable computer 85 which has at its upper portion a display panel (or screen) 87, such as of the LCD type, for displaying the information required by the medication nurse during rounds. The lower portion 89 of the portable computer includes keys used by the nurse for inputting data to the portable computer as well as instructing it to carry out certain operations. On-off button 70 activates the unit or turns power to it OFF. Numerical keys 71-80 enable the entry of numerals as information or commands. The nurse identification code and the patient identification code, for example, are entered with keys 71-80. Key 100 is for the above-described QUERY function. Key 101 is for the GIVEN status while key 102 is for the HOLD status. Keys 103 and 104 are for, respectively, the REFUSE and NOT GIVEN entries. Key 105 is the ENTER button. The portable computer is light and compact so that it can be conveniently hand-carried by the nurse.

It should be readily apparent from all of the above that a highly useful and valuable system has been provided with this invention. Information is entered, processed, retrieved, transmitted, manipulated, updated, and stored electronically with only a minimal intervention, if any, being needed with handwritten information. The potential for error has been significantly reduced, and the convenience to the hospital, the charge nurse, and the medication nurse has been sharply improved. Furthermore, the reliability of the entire medication dispensing operation has been improved as well. Moreover, the technique and hardware are relatively easy to use with minimal training being required for the medication nurse. Although somewhat more training is required for the charge nurse who enters more information into the base computer than the medication nurse enters into the portable computer, nevertheless this training is still comparatively perfunctory.

Besides the many significant advantages available with this invention, the fact that patient information and medication information is electronically resident in a computer data base provides the basis for streamlining and improving several other related services. For example, the hospital keeps all its medicines in a pharmacy. When a physician authorizes that a certain medication be dispensed to a patient, that medication is ordered from the pharmacy. In accordance with the present invention, once the medication information is stored in the base computer, it can be transferred to the pharmacy in electronic form. A handwritten copy of the doctor's prescription can follow so that a verification can be made by the pharmacy to insure accuracy. It is then possible to ascertain which medications are to be dispensed for a given rounds or set of rounds so that the medicines can be collected and sent up to the appropriate floor.

One way of obtaining this result is to search the field in which the frequency of administering the medication is specified. Taking this into account along with the start date and end date for each medication identifies those medications which come up in any given rounds. When the check also includes the building number and room number fields, the pharmacy can determine for each and every floor in the hospital which medications, and how much of each, needs to be sent. This is a very straightforward operation when done in a computer whereas if done by hand with many individual medicine order forms sent to the pharmacy can be labor intensive, complicated, and prone to error.

With the just-described technique made possible by the present invention, it is feasible for the pharmacy to send the medications to the floors in bulk rather than individually packaged. The medication nurses on the floor can then retrieve the medications from the bulk packages and place them individually in cups for each patient. If, however, the pharmacy is proceeding on the basis of individual order forms, to obtain the bulk information is not simple and, therefore, the pharmacy routinely processes these on an individual basis. However, it may be more efficient for the pharmacy to operate in bulk and to have the duty nurses dispense the medication which they do anyway in preparing the dosage for each individual patient. Thus, the operations in the pharmacy are made considerably more efficient in this manner. Of course, the entire process of preparing dosages can be carried out at the pharmacy. In some setups it may be more efficient and more effective to do so rather than taking up nurse time with it.

Inventory control is also facilitated by the present invention. For example, the entire inventory of the pharmacy can readily be stored in a base computer. When the pharmacy distributes medications on order to various hospital floors, the type and quantity of each medication is known since the computer has sent medications that will be given. This can be used to automatically update the inventory data. It is, therefore, unnecessary to have this done laboriously by hand. In fact, the entire operation of taking inventory previously needed is no longer necessary because the base computer performs this operation automatically as the medications are distributed to the hospital floors by the pharmacy.

Billing can also be simplified by taking advantage of the features provided with the present invention. Each patient receives a bill which includes a charge for each of the medications dispensed to him. This information must, of course, be collected so that it can be entered into the bill. This task is also labor intensive and prone to error. Furthermore, the charge for medications varies in accordance with various factors. One of these factors is the category of patient, be it outpatient or admitted patient, or critical care versus alternate care for example. The category of patient is already entered in one of the above-specified patient information fields of the invention. Thus, the pharmacy can have its computer combine the patient category information with the medications specified for that particular patient to provide a listing of all the medications dispensed to that patient. Once that list is accumulated, a multiplication factor is used to calculate that patient's total charges for all the medications dispensed during the hospital stay. The computer can perform this task with little or no additional steps being required beyond those for normal servicing of the pharmacy in its task of dispensing medication. Thus, the billing process is streamlined and its reliability improved.

Another advantage available because of the features provided by the present invention is a report to the physicians warning them that an authorization for a medication previously prescribed is expiring. By keying on the end date field, all the medications which expire on a date a specified number of days hence can be retrieved from the data base in the base computer. These can be retrieved individually for each doctor with a technique which also keys on the doctor field. Thus, each doctor can be supplied with all of the medications which he has authorized and that are about to expire. This is a tremendous help to the hospital and the physicians so that an authorization period is not inadvertently exceeded. Such a situation puts the hospital, nurses and physicians in a very awkward situation when the medication has expired and no replacement authorization exists. By use of this technique, the occurrence of such a situation is rendered highly unlikely. Also, its preparation for review by the physician is quick and easy with the use of the base computer and the data base developed in accordance with this invention.

Printout of accurate, clean, and fully updated reports is also made possible by the electronic storage of pertinent information. For example, the medication summary record discussed above can be quickly and conveniently printed out whenever it is required to provide a clean copy in contrast to the messy, handwritten, and oft-corrected version previously available.

Another feature worthy of mention which has been made available with this invention is the monitoring of various drugs. It is well known that drugs such as narcotics, for example, must be very carefully monitored because of theft. Such monitoring can be done accurately and thoroughly only if it is possible to quickly and easily determine the location where such drugs are supposed to be at any given time. If a manual system is relied upon for this purpose, then a considerable amount of information must be manually reviewed, analyzed, sifted, and reported. However, the computer can do this in a relatively short time. Since the pharmacy has all the necessary information for this purpose stored in its data base, each drug can be readily monitored by simply keying on the particular medication of interest in the medication field. It is then possible to determine which patients have been authorized to receive this medication and, consequently, the hospital floors to which this medication has been sent by the pharmacy. Thus, anyone interested in monitoring the drug inventory on any given floor at a desired time can recall such information from the base computer which will indicate how much of the drug should be present on each hospital floor at any given time.

It is believed that standard, well known computer procedures can be utilized to perform each of the tasks involved in rendering the pharmacy, inventory, billing, and drug monitoring features implementable on a programmable digital computer. Thus, it is not believed that details need be provided.

Although a preferred embodiment has been described above, it should be readily apparent that various modifications to it can readily be made. For example, it is conceivable that rather than completing a chart for the patient when he is first received in admissions, this entry could also be made electronically. The patient information could be transmitted via a local are a network to the head nurse's station on the floor to which the patient is eventually assigned. Likewise, the information could be stored on a diskette and taken by hand to the head nurse's station. Also, the medication instructions issued by the doctor need not be handwritten. The physicians could be trained to enter this information directly into the base computer. Alternatively, the physician could be supplied with a portable computer comparable to that used by the duty nurses. Furthermore, the transmission of information from the portable computer to the base computer can be controlled by a key on the former rather than by a key on the keyboard of the latter. In addition, the nurse could use a bar code reader or touch screen version to enter data into the portable computer. These and other such modifications are intended to fall within the scope of the present invention as defined by the following claims.

We claim:

1. A method for dispensing medication comprising the steps of:
   storing, for each patient, patient information such as the name of the patient which is relevant to the dispensing of medication;
   storing, for each patient, medication information which is directly required for the dispensing of medication including a plurality of prescribed drugs and corresponding respective dosages, frequency for administering each of the plurality of prescribed drugs, time period and dates during which a prescription order for each drug is valid, and conditions relevant to dispensation of a particular medication to a particular patient under particular circumstances;
   said patient information and said medication information for a plurality of patients being stored into a memory of a stationary base computer;
   retrieving from said memory at least some of said patient information and said medication information for, respectively, designated ones of said plurality of patients;
   transferring said retrieved patient information and said retrieved medication information to a portable computer adapted to be carried by as nurse assigned the task of dispensing medication to said designated patients;
   inputting the data and time of a medication dispensing rounds;
   identifying patients from among the designated patients and the prescribed drugs scheduled to be dispensed thereto during said rounds by processing with the portable computer the retrieved patient and medication information transferred to the portable computer through selection of information based at least on the time of said rounds along with the frequency, time period and date medication information; and for each of the identified patients, in sequence, displaying the processed information to said nurse in the form of only that medication information required by the nurse to identify the drugs scheduled to be dispensed during said rounds and the corresponding relevant conditions;

whereby, for said rounds, the nurse is sequentially apprised of all patients assigned to said nurse, all medications scheduled for dispensing to each of the assigned patients, and all the conditions relevant to the respective dispensation of each medication to each patient under particular circumstances.

2. The method of claim 1, further comprising the step of storing into said portable computer a medication dispensation status data for at least one of said medications to record whether the medication scheduled for each patient was administered.

3. The method of claim 2, further comprising the step of transferring the medication dispensation status entered into the portable computer from said portable computer to the base computer to update the medication information stored therein.

4. The method of claim 3, further comprising the step of assigning a set of designated patients for each nurse, and wherein said transferring step comprises transferring to one portable computer retrieved patient information and retrieved medication information for only those designated patients assigned to one nurse.

5. The method of claim 4, further comprising the steps of storing a unique code for each nurse in the base computer, transferring said code to the portable computer, and restricting operation of the portable computer unless the correct code for a given nurse is entered into the portable computer.

6. The method of claim 5, further comprising the step of verifying the identity of a patient before the prompting step is performed.

7. The method of claim 6, wherein the patient information includes a unique identification code for each patient, and wherein the identity verification step comprises entering into the portable computer a number from an identity bracelet attached to the patient's wrist, retrieving from the patient information stored in said portable computer a name corresponding to such number, and displaying said name on the portable computer.

8. The method of claim 7, wherein said prompting step comprises displaying patient information and medication information on a display panel in said portable computer.

9. The method of claim 8, further comprising the step of comparing the medication information stored in said portable computer with the medication dispensation status information stored in the portable computer to determine whether any medications have not been administered.

10. The method of claim 9, further comprising the step of notifying said nurse with the portable computer those of the medications to be dispensed which have not been dispensed.

11. The method of claim 10, wherein said notifying step comprises displaying to the nurse each missed medication.

12. The method of claim 10, further comprising the steps of storing in said portable computer data on those medications not administered when a given rounds is completed, transferring said data on those medications which were not administered to said base computer, and then transferring such data back to said portable computer in preparation for conducting rounds immediately following said given rounds, wherein said notifying step occurs at the beginning of said following rounds for medications not dispensed during the given rounds.

13. The method of claim 12, wherein said notifying step is performed at the beginning of rounds for medications not dispensed during the previous rounds and then during a rounds for medications not dispensed during the rounds in progress.

14. The method of claim 10, wherein said notifying step occurs during a rounds for medications not dispensed during the rounds in progress.

15. The method of claim 14, further comprising the steps of transferring medication information to a pharmacy and supplying for each rounds from said pharmacy all the required medication based on such transferred medication information to the pharmacy.

16. The method of claim 15, wherein said transferred medication information to the pharmacy is combined with electronically stored medical supplies inventory data at the pharmacy to update said inventory data.

17. The method of claim 16, wherein the status data is combined with electronically stored medical supplies inventory data to update said inventory data.

18. The method of claim 17, wherein data on said status is combined with electronically stored billing data to update said billing data.

19. The method of claim 18, further comprising the steps of transferring the information stored in said portable computer to said base computer to update the information stored in said base computer.

20. The method of claim 10, further comprising the step of storing in said portable computer data on those medications not administered when a given rounds is completed, transferring said data on those medications which were not administered to said base computer, and then transferring such data back to said portable computer in preparation for conducting rounds immediately following said given rounds, wherein said notifying step occurs at the beginning of said following rounds for medications not dispensed during the given rounds.

21. The method of claim 20, wherein said notifying step is performed at the beginning of rounds for medications not dispensed during the previous rounds and then during a rounds for medications not dispensed during the rounds in progress.

22. The method of claim 1, further comprising the step of assigning a set of designated patients for each nurse, and wherein said transferring step comprises transferring to one portable computer retrieved patient information and retrieved medication information for only those designated patients assigned to one nurse.

23. The method of claim 1, further comprising the steps of storing a unique code for each nurse in the base computer, transferring said code to the portable computer, and restricting operation of the portable computer unless the correct code for a given nurse is entered into the portable computer.

24. The method of claim 1, further comprising the step of verifying the identity of a patient before the prompting step is performed.

25. The method of claim 24, wherein the patient information includes a unique identification code for each patient, and wherein the identity verification step comprises entering into the portable computer a number from an identity bracelet attached to the patient's wrist, retrieving from the patient information stored in said portable computer a name corresponding to such number, and displaying said name on the portable computer.

26. The method of claim 1, wherein said prompting step comprises displaying patient information and medication information on a display panel in said portable computer.

27. The method of claim 1, further comprising the step of comparing the medication information stored in said portable computer with the status information stored in the portable computer to determine whether any medications have not been administered.

28. The method of claim 27, further comprising the step of notifying said nurse with the portable computer those of the medications to be dispensed which have not been dispensed.

29. The method of claim 28, wherein said notifying step comprises displaying to the nurse each missed medication.

30. The method of claim 28, wherein said notifying step occurs during a rounds for medications not dispensed during the rounds in progress.

31. The method of claim 1, further comprising the steps of transferring medication information to a pharmacy and supplying for each rounds from said pharmacy all the required medication based on such transferred medication information to the pharmacy.

32. The method of claim 1, further comprising the steps of transferring the information stored in said portable computer to said base computer to update the information stored in said base computer.

33. A method for dispensing medication comprising the steps of:
    storing, for each patient, patient information such as the name of the patient which is relevant to the dispensing of medication;
    storing, for each patient, medication information which is directly required for the dispensing of medication including a plurality of prescribed drugs and corresponding respective dosages, frequency for administering each of the plurality of prescribed drugs, time period and dates during which a prescription order for each drug is valid, and conditions relevant to dispensation of a particular medication to a particular patient under particular circumferences;
    said patient information and said medication information for a plurality of patients being stored into a memory of a portable, hand-held computer adapted to be carried by a nurse assigned the task of dispensing medication to said plurality of patients;
    inputting the date and time of a medication dispensing rounds;
    identifying patients from among the plurality of patients and the prescribed drugs scheduled to be dispensed thereto during said rounds by processing with the portable computer the stored patient and medication information through selection of information based at least on the time of said rounds along with the frequency, time period, and date medication information; and
    for each of the identified patients, in sequence, displaying the processed information to said nurse in the form of only that medication information required by the nurse to identify the drugs scheduled to be dispensed during said rounds and the corresponding relevant conditions;
    whereby, for said rounds, the nurse is sequentially apprised of all patients assigned to said nurse, all medications scheduled for dispensing to each of the assigned patients, and all the conditions relevant to the respective dispensation of each particular medication to each particular patient under particular circumstances.

34. The method of claim 33, wherein said selectively prompting step comprises the step of displaying the name of a patient along with the medication information for such patient.

35. The method of claim 34, wherein the displayed medication information includes the name of a medication to be dispensed, dose and route.

36. The method of claim 35, further comprising the step of storing into said portable computer the medication dispensation status for at least one of said medications to record whether the medication scheduled for each patient was administered.

37. The method of claim 36, further comprising the step of verifying the identity of a patient before the prompting step is performed.

38. The method of claim 37, wherein the patient information includes a unique identification code for each patient, and wherein the identity verification step comprises entering into the portable computer a number from an identity bracelet attached to the patient's wrist, retrieving from the patient information stored in said portable computer a name corresponding to such number, and displaying said name on the portable computer.

39. The method of claim 38, further comprising the step of comparing the medication information stored in said portable computer with the medication dispensation status information stored in the portable computer to determine whether any medications have not been administered.

40. The method of claim 39, further comprising the step of notifying said nurse with the portable computer those of the medications to be dispensed which have not been dispensed.

41. The method of claim 33, further comprising the step of notifying said nurse with the portable computer those of the medications to be dispensed which have not been dispensed.

42. The method of claim 41, wherein said notifying step comprises displaying to the nurse each missed medication.

43. The method of claim 42, further comprising the step of storing in said portable computer data on those medications not administered when a given rounds is completed, transferring said data on those medications which were not administered to said base computer, and then transferring such data back to said portable computer in preparation for conducting rounds immediately following said given rounds, wherein said notifying step occurs at the beginning of said following rounds for medications not dispensed during the given rounds.

44. The method of claim 43, wherein said notifying step is performed at the beginning of rounds for medications not dispensed during the previous rounds and then during a rounds for medications not dispensed during the rounds in progress.

45. The method of claim 41, wherein said notifying step occurs during a rounds for medications not dispensed during the rounds in progress.

46. Apparatus for guiding a nurse in the activity of dispensing medication comprising:

means for storing, for each patient of a plurality of patients, patient information such as the name of the patient which is relevant to the dispensing of medication;

means for storing, for each patient of said plurality of patients, medication information which is directly required for the dispensing of medication including a plurality of prescribed drugs and corresponding respective dosages, frequency for administering each of the plurality of prescribed drugs, time period and dates during which a prescription order for each drug is valid, and conditions relevant to dispensation of a particular medication to a particular patient under particular circumstances;

said patient information storing means and said medication information storing means being comprised in a memory of a stationary base computer;

means for retrieving from said memory at least some of said patient information and said medication information for, respectively, designated ones of said plurality of patients;

portable computer means adapted to be carried by a nurse assigned the task of dispensing medication to said designated patients;

means for transferring said retrieved patient information and said retrieved medication information to said portable computer means;

means for inputting the date and time of a medication dispensing rounds;

said portable computer including:
  means for identifying patients from among the designated patients and the prescribed drugs scheduled to be dispensed thereto during said rounds by processing with the portable computer the retrieved patient and medication information transferred to the portable computer through selection of information based at least on the time of said rounds along with the frequency, time period, and date medication information; and
  means for displaying the processed information to said nurse for each of the identified patients, in sequence, in the form of only that medication information required by the nurse to identify the drugs scheduled to be dispensed during said rounds and the corresponding relevant conditions;

whereby, for said rounds, the nurse is sequentially apprised of all patients assigned to said nurse, all medications scheduled for dispensing to each of the assigned patients, and all the conditions relevant to the respective dispensation of each particular medication to each particular patient under particular circumstances.

47. The apparatus of claim 46, further comprising means for storing into said portable computer means a medication dispensation status data for at least one of said medications to record whether the medication scheduled for each patient during rounds in progress was administered.

48. The apparatus of claim 47, further comprising means for transferring the medication dispensation status entered into the portable computer means from said portable computer means to the base computer to update the medication information stored therein.

49. The apparatus of claim 47, further comprising means for assigning a set of designated patients for each nurse, and wherein said transferring means comprises further means for transferring to one portable computer means unit the retrieved patient information and retrieved medication information for only those designated patients assigned to one nurse.

50. The apparatus of claim 49, further comprising means for storing a unique code for each nurse in the base computer, means for transferring said code to the portable computer means, and means for restricting operation of the portable computer means unless the correct code for a given nurse is entered into the portable computer means.

51. The apparatus of claim 50, further comprising means for verifying the identity of a patient.

52. The apparatus of claim 51, wherein the patient information includes a unique identification code for each patient, and wherein the identity verification means comprises means for entering into the portable computer means a number from an identity bracelet attached to the patient's wrist, means for retrieving from the patient information stored in said portable computer means a name corresponding to such number, and means for displaying said name on the portable computer means.

53. The apparatus of claim 52, wherein said prompting means comprises means for displaying patient information and medication information on a display panel in said portable computer means.

54. The apparatus of claim 53, further comprising means for comparing the medication information stored in said portable computer means with the medication dispensation status information stored in the portable computer means to determine whether any medications have not been administered.

55. The apparatus of claim 54, further comprising means for notifying said nurse with the portable computer means those of the medications to be dispensed which have not been dispensed.

56. The apparatus of claim 55, wherein said notifying means comprises means for displaying to the nurse each missed medication.

57. The apparatus of claim 55, further comprising means for storing in said portable computer means data on those medications not administered when a given rounds is completed, transferring said data on those medications which were not administered to said base computer, and then transferring such data back to said portable computer means in preparation for conducting rounds immediately following said given rounds, wherein said notifying means operates at the beginning of said following rounds for medications not dispensed during the given rounds.

58. The apparatus of claim 57, wherein said notifying means operates at the beginning of rounds for medications not dispensed during the previous rounds and then during a rounds for medications not dispensed during the rounds in progress.

59. The apparatus of claim 55, wherein said notifying means operates during a rounds for medications not dispensed during the rounds in progress.

60. The apparatus of claim 46, further comprising means for assigning a set of designated patients for each nurse, and wherein said transferring means comprises further means for transferring to one portable computer means retrieved patient information and retrieved medication information for only those designated patients assigned to one nurse.

61. The apparatus of claim 46, further comprising means for storing a unique code for each nurse in the base computer means transferring said code to the portable computer, and restricting operation of the portable computer unless the correct code for a given nurse is entered into the portable computer.

62. The apparatus of claim 46, further comprising means for verifying the identity of a patient.

63. The apparatus of claim 62, wherein the patient information includes a unique identification code for each patient, and wherein the identity verification means comprises means for entering into the portable computer means a number from an identity bracelet attached to the patient's wrist, retrieving from the patient information stored in said portable computer means a name corresponding to such number, and means for displaying said name on the portable computer means.

64. The apparatus of claim 46, wherein said prompting means comprises means for displaying patient information and medication information on a display panel in said portable computer means.

65. The apparatus of claim 46, further comprising means for comparing the medication information stored in said portable computer means with the status information stored in the portable computer means to determine whether any medications have not been administered.

66. The apparatus of claim 65, further comprising means for notifying said nurse with the portable computer means those of the medications to be dispensed which have not been dispensed.

67. The apparatus of claim 66, wherein said notifying means comprises means for displaying to the nurse each missed medication.

68. The apparatus of claim 66, further comprising means for storing in said portable computer means data on those medications not administered when a given rounds is completed, transferring said data on those medications which were not administered to said base computer, and then transferring such data back to said portable computer means in preparation for conducting rounds immediately following said given rounds, wherein said notifying means operates at the beginning of said following rounds for medications not dispensed during the given rounds.

69. The apparatus of claim 68, wherein said notifying means operates at the beginning of rounds for medications not dispensed during the previous rounds and then during a rounds for medications not dispensed during the rounds in progress.

70. The apparatus of claim 66, wherein said notifying means operates during a rounds for medications not dispensed during the rounds in progress.

71. The apparatus of claim 46, further comprising means for transferring the information stored in said portable computer means to said base computer means to update the information stored in said base computer.

72. Apparatus for dispensing medication comprising:
means for storing, for each patient of a plurality of patients, patient information such as the name of the patient which is relevant to the dispensing of medication;
means for storing, for each patient of said plurality of patients, medication information, such as the name of the medication, which is directly required for the dispensing of medication including a plurality of prescribed drugs and corresponding respective dosages, frequency for administering each of the plurality of prescribed drugs, time period and dates during which a prescription order for each drug is valid, and conditions relevant to dispensation of a particular medication to a particular patient under particular circumstances;
said patient information means and said medication information means being comprised in a memory of a portable, hand-held computer adapted to be carried by a nurse assigned the task of dispensing medication to said designated patients, said portable computer including:
means for inputting the data and time of a medication dispensing rounds;
means for identifying patients from among the plurality of patients and the prescribed drugs scheduled to be dispensed thereto during said rounds by processing the stored patient and medication information through selection of information based at least on the time of said rounds along with the frequency, time period and date medication information; and
means for displaying the processed information to said nurse for each of the identified patients, in sequence, in the form of only that medication information required by the nurse to identify the drugs scheduled to be dispensed during said rounds and the corresponding relevant conditions;
whereby, for said rounds, the nurse is sequentially apprised of all patients assigned to said nurse, all medications scheduled for dispensing to each of the assigned patients, and all the conditions relevant to the respective dispensation of each particular medication to each particular patient under particular circumstances.

73. The apparatus of claim 72, wherein said selectively prompting means comprises means for displaying the name of a patient along with the medication information for such patient.

74. The apparatus of claim 73, wherein the displayed medication information includes the name of a medication to be dispensed, dose and route.

75. The apparatus of claim 74, further comprising means for storing into said portable computer the medication dispensation status for at least one of said medications to record whether the medication scheduled for each patient was administered.

76. The apparatus of claim 75, further comprising means for verifying the identity of a patient.

77. The apparatus of claim 76, wherein the patient information includes a unique identification code for each patient, and wherein the identity verification means comprises means for entering into the portable computer a number from an identity bracelet attached to the patient's wrist, retrieving from the patient information stored in said portable computer a name corresponding to such number, and displaying said name on the portable computer.

78. The apparatus of claim 77, further comprising means for comparing the medication information stored in said portable computer with the medication dispensation status information stored in the portable computer to determine whether any medications have not been administered.

79. The apparatus of claim 78, further comprising means for notifying said nurse with the portable computer those of the medications to be dispensed which have not been dispensed.

80. The apparatus of claim 72, further comprising means for notifying said nurse with the portable computer those of the medications to be dispensed which not been dispensed.

81. The apparatus of claim 80, wherein said notifying means comprises means for displaying to the nurse each missed medication.

82. The apparatus of claim 80, further comprising means for storing in said portable computer data on those medications not administered when a given rounds is completed, transferring said data on those medications which were not administered to said base computer, and then transferring such data back to said portable computer in preparation for conducting rounds immediately following said given rounds, wherein said notifying means operates at the beginning of said following rounds for medications not dispensed during the given rounds.

83. The apparatus of claim 82, wherein said notifying means operates at the beginning of rounds for medications not dispensed during the previous rounds and then during a rounds for medications not dispensed during the rounds in progress.

84. The apparatus of claim 80, wherein said notifying means operates during a rounds for medications not dispensed during the rounds in progress.

* * * * *